Figure 1A:
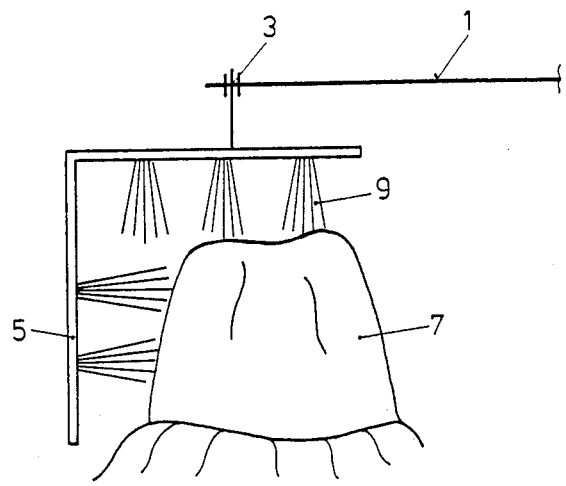

United States Patent [19]

Maurer

[11] Patent Number: 4,795,347

[45] Date of Patent: Jan. 3, 1989

[54] PROCESS AND DEVICE FOR THE CLEANING OF TEETH

[76] Inventor: Wilhelm Maurer, Talacherring 15, 8103 Unterengstringen, Switzerland

[21] Appl. No.: 771,713

[22] Filed: Sep. 3, 1985

[30] Foreign Application Priority Data

Aug. 31, 1984 [DE] Fed. Rep. of Germany ....... 3431991

[51] Int. Cl.⁴ .............................................. A61K 5/00
[52] U.S. Cl. .................................... 433/216; 15/22 R; 128/62 A
[58] Field of Search .............. 15/167 A, 167 R, 22 R; 128/62 A, 24 A; 433/216; 134/6

[56] References Cited

U.S. PATENT DOCUMENTS

| | | | |
|---|---|---|---|
| 2,628,377 | 2/1953 | Cockriel | 15/23 |
| 2,935,755 | 5/1960 | Leira et al. | 15/167 R |
| 3,440,680 | 4/1967 | Werding | 15/321 |
| 3,592,188 | 7/1971 | Barnett | 128/62 A |
| 3,683,442 | 8/1972 | Holly | 15/167 R |
| 4,223,417 | 9/1980 | Solow | 15/22 R |
| 4,224,710 | 9/1980 | Solow | 15/22 R |
| 4,346,492 | 8/1982 | Solow | 15/22 R |
| 4,377,877 | 3/1983 | O'Rourke | 15/4 |
| 4,545,087 | 10/1985 | Nahum | 15/22 R |

Primary Examiner—Gene Mancene
Assistant Examiner—Adriene J. Lepiane
Attorney, Agent, or Firm—Antonelli, Terry & Wands

[57] ABSTRACT

A tooth cleaning device for optimal tooth cleaning comprises, on a U-shaped carrier (109), tufts of bristles (180), which are placed against the tooth using pressure bubbles (149) under equal cleaning pressure on both sides. With this arrangement the tufts of bristles (180) are fitted to individually self-positioning rocker arms (174, 178'), in order to also engage in the spaces between the teeth, which are difficult to access. With the aid of a further pressure bubble arrangement (147) using phase-shifted pulsating pressurization, with reference to the pressure-generating bubbles (149), a wiping movement of the tufts of bristles (180) with cleaning pressure is generated in the direction from the gum towards the crown of the tooth, in counter-direction without bearing pressure on the tooth.

49 Claims, 14 Drawing Sheets

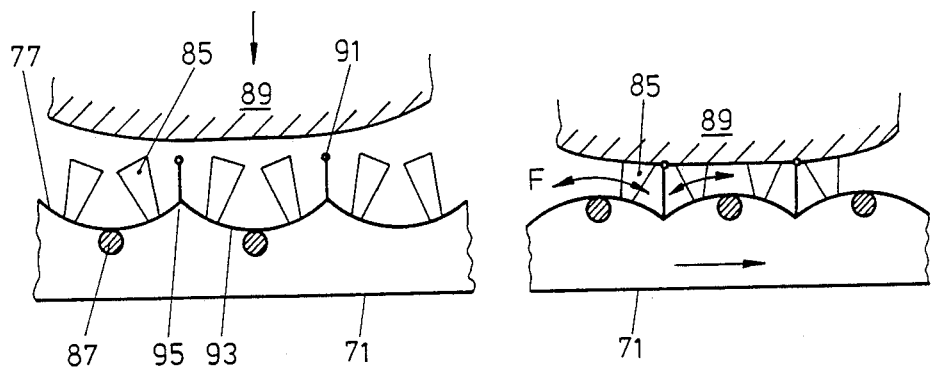
FIG. 9
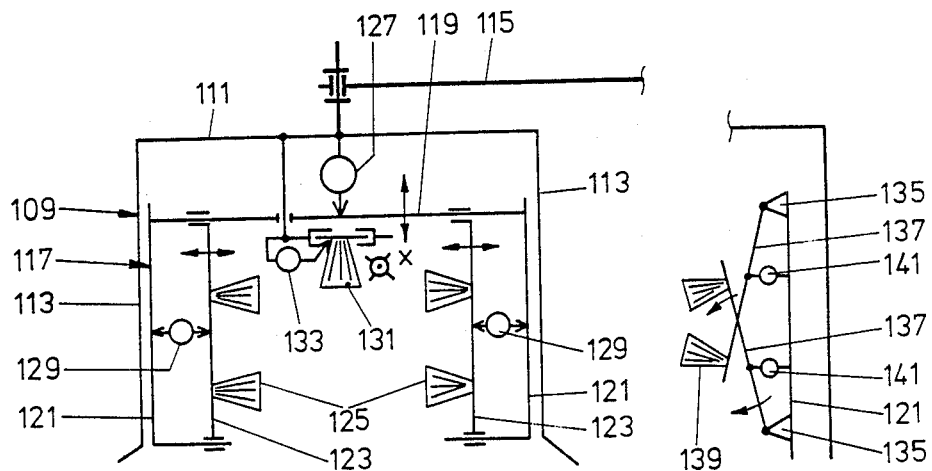
FIG. 10
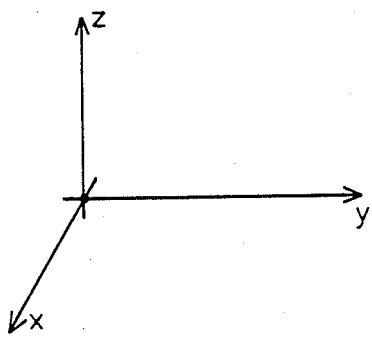

PROCESS AND DEVICE FOR THE CLEANING OF TEETH

The present invention relates to processes for cleaning teeth by means of a device and to tooth cleaning devices, whereby driven cleaning means are provided, drive operated in a first direction corresponding to a tooth longitudinal axis, and in a second direction, vertical thereto, corresponding to a direction from the tooth longitudinal axis toward tongue and cheek areas, respectively, with the cleaning means movement describing a closed path in a plane set by the first and second directions, with a tooth comb device including at least one cleaning means supported against a reference arrangement in such a manner that at least one cleaning surface of the cleaning means can move along a closed, at least planar movement path with driving means for driving the cleaning means.

Dental care can be effected in various ways which partially complement each other. Up to now the brushing of teeth has proved the best method. Of great importance is the removal of the so-called plaque for preventing cavities and also a meaningful massage of the gum. Investigations have shown that when using conventional cleaning devices such as tooth brushes the inner face of the teeth, i.e. the side facing the oral cavity is not cleaned nearly as well as the outer face of the teeth, with the faces defining the interdental gap being even worse off. One reason for this must certainly be seen in the fact that it is much more difficult to guide a tooth cleaning device such as a tooth brush on the inner face of the teeth. Teeth should however be cleaned equally well on the inner surface as well as on the outer surface and also in the interdental gap. Furthermore it has been scientifically proven that cleaning means such as bristles should perform a pushing movement starting from the gum via the neck of the tooth to the crown of the tooth. Also, with conventional tooth cleaning devices, cleaning contact pressure between the cleaning means and the tooth is completely arbitrary. If pressure is insufficient, cleaning quality is poor. If on the other hand, pressure is excessive, this may impair the gum/tooth and the tooth enamel, and in particular the gum base at the neck of the tooth. Therefore conventional tooth cleaning devices have the following disadvantages:

(a) Equally good cleaning of two tooth surfaces is difficult, in particular where the inner surface, i.e. the surface facing the oral cavity and the outer surface, i.e. the surface facing the cheek, or the surfaces defining the interdental gap are concerned.

(b) The application of optimal local cleaning pressure is not ensured.

(c) During cleaning the optimal movements of the cleaning means away from the gum in tooth-axial direction towards the crown of the tooth do not occur essentially less frequently than the opposite movements.

It is therefore the requirement of the current invention to create processes of the kind mentioned in the beginning and appropriate cleaning devices which make it possible to eliminate the disadvantages (a) or (b) or (c) or all possible combinations of these disadvantages, in other words that at least one of the following objectives is achieved:

(A) Cleaning of the teeth on their side faces, in particular on their inner and outer faces as well as on the faces defining the interdental gap shall be easy to achieve and/or (B) the cleaning pressure shall be controlled and/or (C) the cleaning means shall be moved in an optimal movement from the gum to the crown of the tooth.

To meet requirement (A) a process of the kind mentioned above is characterised in that cleaning is effected simultaneously on at least two faces of the tooth.

Correspondingly a tooth cleaning device for meeting this part of the requirement is characterised in that when viewed from the direction of a tooth, a concavely arched carrier section is provided including cleaning elements for embracing the teeth on at least two sides.

Requirement part (B) is met by a process of the kind mentioned above which is characterised in that cleaning of a tooth surface area is effected under controlled cleaning pressure, preferably at a pre-set pressure.

Correspondingly a tooth cleaning device for meeting requirement part (B) is characterised in that a carrier section is provided as a reference system and in that cleaning elements are provided on the carrier section via pressure controlling means.

Requirement part (C) in turn, is met by a process of the kind mentioned above which is characterised in that cleaning is effected under cleaning pressure from the gum towards the tooth area with the return movement in the direction of the gum being effected at at least lesser pressure.

The tooth cleaning device for meeting requirement part (C) is characterised in that driven cleaning elements are provided, such, that one movement of the cleaning elements is carried out under cleaning pressure from the root of the tooth to the crown of the tooth with the return movement being carried out under at least reduced cleaning pressure.

Combinations of the requirement parts (A) to (C) to be met are achieved by combinations of the said process and device characteristics.

To met the requirement whereby inner and outer cleaning shall be as even as possible, it is suggested in one embodiment that the teeth on opposite sides be contacted with the cleaning elements under at least approximately equal pressures.

The above mentioned third part of the requirement, i.e. the optimal cleaning pushing movement of the cleaning elements away from the root of the tooth in longitudinal direction of the tooth, which, among others, also leads to a good massage of the gum, is met in one embodiment, in that contacting is carried out cyclically on both sides by starting in the area of the gum under increased, at least approximately equal pressure on both sides, by then moving the contacting area away from the area of the gum in at least one component linearly along the teeth, thereafter at least reducing the pressure and returning the contacting area into its original position.

The above mentioned optimal massage and cleaning movement is achieved by this cyclic movement, synchronous with the raising or lowering of the contacting pressure between device and tooth. It is further suggested for one embodiment, that the teeth be further contacted with cleaning elements on their top face. This would preferably be accompanied by moving their contacting area on the top of the tooth, preferably cyclically back and forth and preferably at least in one component vertically to the side faces of the tooth. This means a cleaning, cyclic reciprocal movement of cleaning elements for the top of the teeth simultaneously with the above mentioned cleaning arrangements for the side faces.

If, according to one embodiment contacting is effected with several individually self-positioning areas due to the tooth reaction forces, optimal moulding of the cleaning elements to the respective tooth surfaces is ensured on both sides of the teeth including individual tooth shapes, in particular good cleaning is made possible in the interdental gap, generally in hardly accessible or difficult-to-access areas such as crevices etc.

A tooth cleaning device, initially for meeting the first part of the requirement, i.e. for facilitating cleaning of the teeth on both sides, comprises, in one embodiment, a U-shaped carrier section with cleaning elements facing inwards on at least the sides.

To enable the user to readily guide the said tooth cleaning device along the teeth, it is suggested in a further development of the device, that the U-shaped holder be movably mounted in particular be at least pivotably mounted, resulting in the carrier section adapting its position automatically to the position of the teeth, with easy guiding on the guiding grip.

In order to influence the cleaning contacting pressure between cleaning elements and teeth, it is further suggested that the cleaning elements be arranged on the sides of the U via pressure generating elements. The pressure generating elements are easily formed by a bellows or bubble arrangement, preferably a plastic bubble arrangement. If the bubble arrangements which are preferably driven hydraulically or pneumatically such as by air or by water, are designed so as to communicate with each other, equal cleaning contact pressure is automatically generated on each U-side and thus on both sides of a tooth to be cleaned. Further provided pre-tensioning elements on the bubble arrangements bring about or support, on the one hand, a recovery of the bubbles when pressure is relieved, and on the other hand, a pre-set initial pressure, i.e. the pressure acting upon the tooth is raised or lowered, according to the pre-tensioning direction, by the initial pressure of the pre-tensioning elements, with reference to the pressure of the medium, such as the air or water pressure in the bubbles.

Due to the fact that the cleaning elements are arranged so as to be linearly movable in at least one component in U-side direction, it is possible to shift the cleaning elements in axial direction of the tooth, be it driven or automatically. In the latter case movement in one direction may be made against a damper, such as a spring, in moving direction away from the U-base of the carrier section—thus from the root of the tooth towards the crown of the tooth—whilst the counter movement is less dampened or unrestricted. Thus the above mentioned optimal wiping movement from the root of the tooth towards the crown of the tooth is realized by successive placing and withdrawing of the device. If driving elements are provided for the cyclic movement of the cleaning elements, these will take over control of the cleaning element movement in the above mentioned optimal sense, possibly in cooperation with the pressure generating elements.

In the U-plane of the carrier-section the cleaning elements perform preferably closed, preferably two-dimensional movement paths, whereby sides of the path directed against the U-axis of symmetry are passed through in the direction of the U-base, which, in turn, results in the above mentioned optimal movement, whilst during the return movement the cleaning elements more or less cease to have contact with the gum and crown of the tooth. In one embodiment of the device this movement is controlled in that the cleaning elements are arranged respectively on one of the U-sides via pressure-generating elements, in that the cleaning elements are movable in at least one component in U-side direction and in at least one component vertically thereto, and in that drive elements are provided at least for the movement of the cleaning elements in U-side direction, in that further the pressure-generating elements and the drive elements control the pressure or the movement cyclically with pre-set phase-shift. The pressure generating elements will then generate, without inserted tooth, i.e. without pressure reaction, a movement parallel to the U-base of the holder, whilst the drive elements control the movement parallel to the U-sides and, with corresponding phase-shift of these two initially independent movements, cyclic movement figures are performed in the U-plane, similar to Lissajous figures. The performance of the movement vertical to the sides of the U-carrier-section and, in particular, the mounting of the thus moved cleaning elements become simple for example, by pivotably mounting the cleaning elements on the sides on at least approximately baseplane-parallel axes. If with this arrangement, the cleaning elements on each of the sides are pivotably mounted partly about axes mounted at the far end of the side and partly about axes mounted at the other end near the base, this results, for a pivotal movement about said axes, in a pincer-type contacting of the tooth surfaces by the cleaning elements. This mounting is easily realized in that, for example, the cleaning elements are arranged on rocker arms, which in turn are mounted on the axes. With this arrangement pressure generating elements are preferably provided between each side and the rocker arms, preferably a bubble arrangement such as a plastic bubble arrangement. In order to realize a cleaning element movability both vertically to the base of the U-carrier-section and vertically to its sides, it is suggested in one embodiment that the cleaning elements on the sides be mounted via a carrier arrangement movable in longitudinal direction of the sides. In order to further provide constructionally for individually self-positioning cleaning elements arranged as closely as possible along the sides, it is further suggested that on each side, first rocker arms, with cleaning elements, be pivotably mounted at the far end of the side and second rocker arms lying in between be pivotably mounted near the base, also equipped with cleaning elements. With this arrangement the first and second rocker arms may mesh with each other in comblike fashion, being pivotably mounted on respectively opposite sides. Thus an optimal covering of the tooth surfaces by means of contacting cleaning elements such as bristle tufts is achieved during use, such as with the said pressure generating elements which act between sides and rocker arms. A further variant aimed, on the one hand, at restoring the pressure generating elements whilst releasing the tooth, and on the other, at individually adapting the cleaning elements to the momentary position of their contacting areas with the tooth, is achieved in that the cleaning elements are, if need be, arranged on or above the pressure-generating elements by means of a flexible carrier, preferably rubber-elastic, such as a nap structure. If this carrier is a relatively voluminous, i.e. a thick rubber-elastic mat, it may be used additionally or exclusively to ensure that the cleaning elements individually mold themselves to the tooth surfaces, even if the pressure generating elements act relatively rigid only in U-base-parallel direction. If, however, the pressure generating elements are formed by flexible bellows such as plastic bubbles, the flexible carrier may be tensioned like a rubber-elastic skin over the bubbles, and carry the cleaning elements. This skin will then act as a resetting element for the bubbles on the one hand, and on the other, allow the cleaning elements, such as bristle tufts, to mold to the teeth. To complement all design variants mentioned, it is suggested, for the simultaneous cleaning of the top face of the tooth, that cleaning elements be also arranged on the U-base. In a further development drive elements are provided again for moving these cleaning elements in at least one component linearly in one plane parallel to the U-base. These cleaning elements thus wipe over the tooth surface, whereby pressure generating elements may be provided if wished. The pressure generating elements may be bellows or bubbles or also spring elements, in which case the carrier arrangement is preferably movably mounted at least in the direction of its base thus resulting in an equilibrium of forces at the inserted tooth, which happens only if the reaction forces on both sides of the tooth are equal. Such an arrangement is preferably realized by means of a rubber-elastic intermediate layer between spring elements and cleaning elements, resulting not only in an equilibrium of forces on both sides but also in a uniform distribution of pressure on both sides of the tooth. A further embodiment for an optimal movement of the cleaning elements along the teeth is derived in that the cleaning elements comprise cleaning rollers on the U-sides, preferably with tangential speed in opposing peripheral areas, directed towards the base. If the rollers are non-driven or gear-driven, they run in that direction in which the opposing peripheral areas have tangential speeds away from the base, against a relatively great damping, practically undampened in reverse—such as realized by a ratchet system—thereby allowing the cleaning device to be placed on the teeth without resistance and to be withdrawn again against the damping resistance away from the gum towards the crown of the tooth.

Figure 1B:
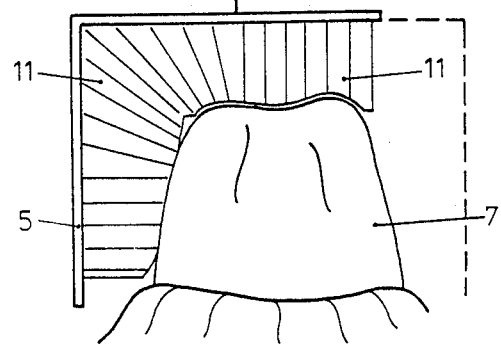
Figure 1C:
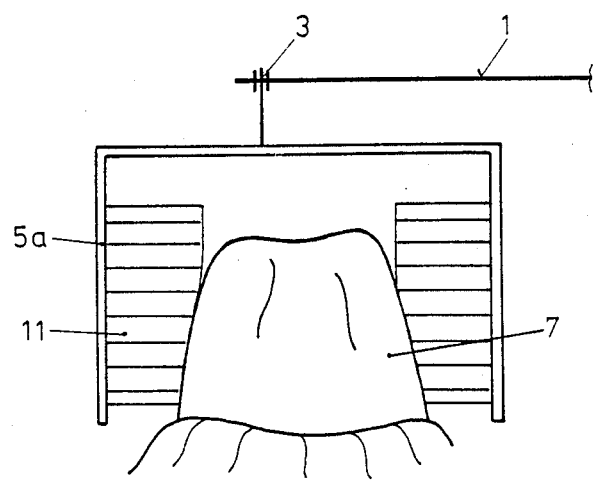
Figure 2A:
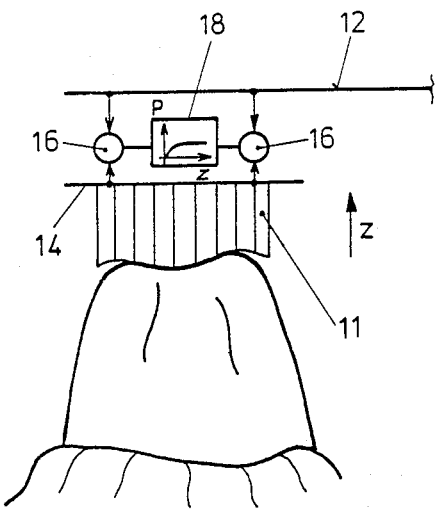
Figure 2B:
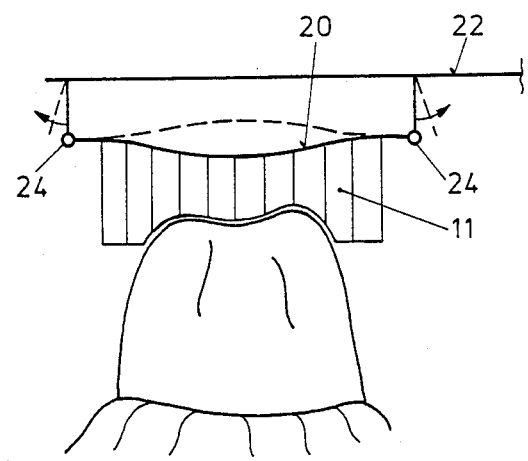
Figure 2C:
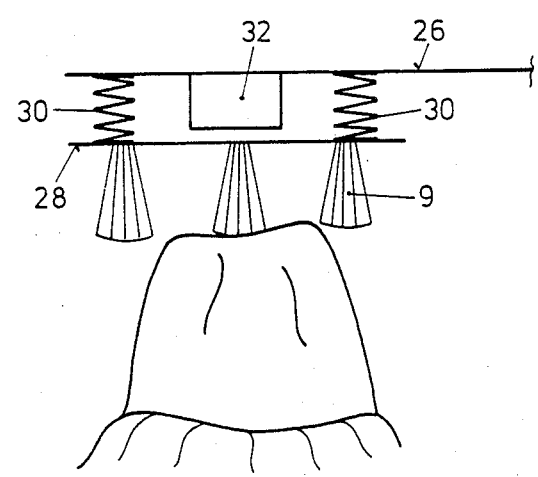
Figure 3A:
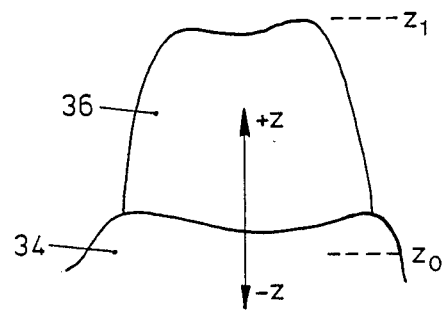
Figure 3B:
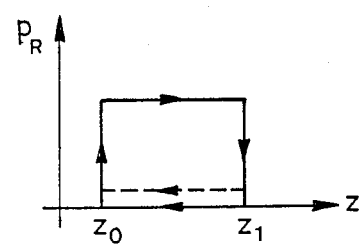
Figure 4:
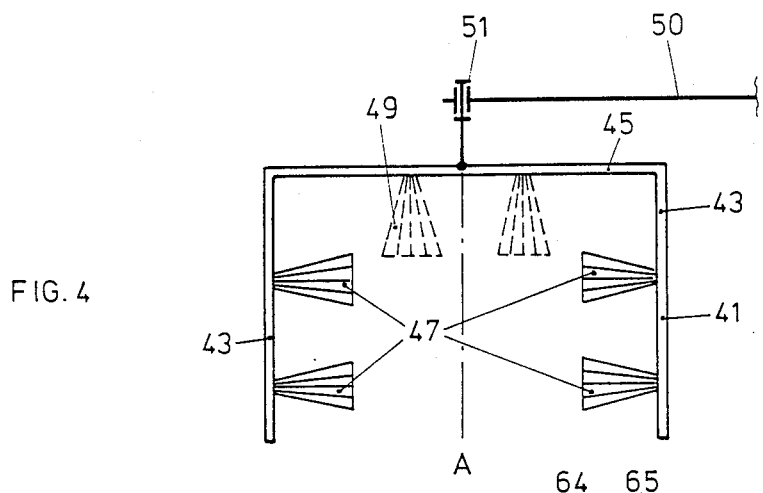
Figure 5:
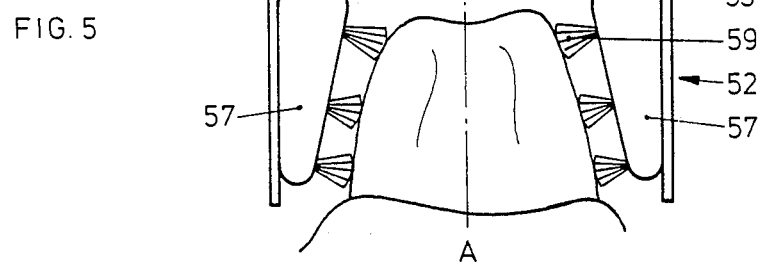
Figure 6:
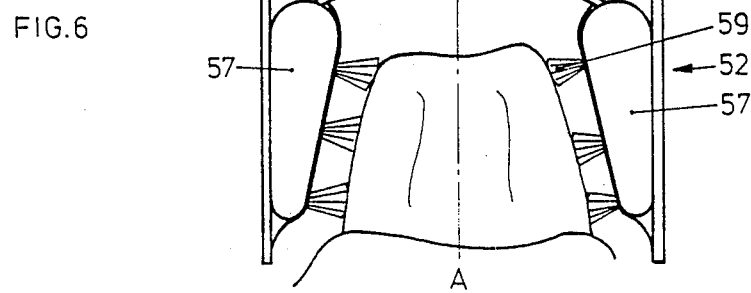
Figure 7:
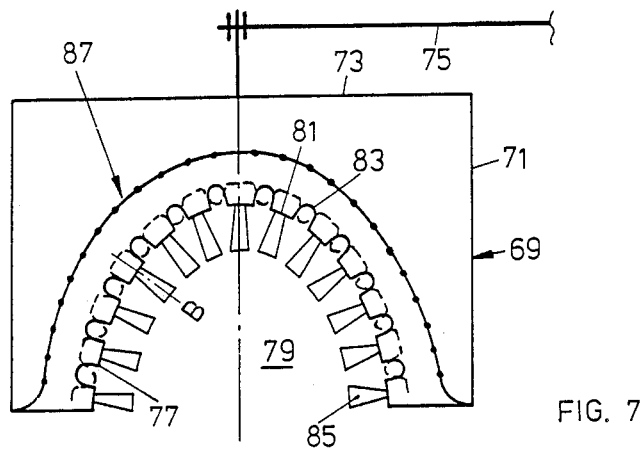
Figure 8:
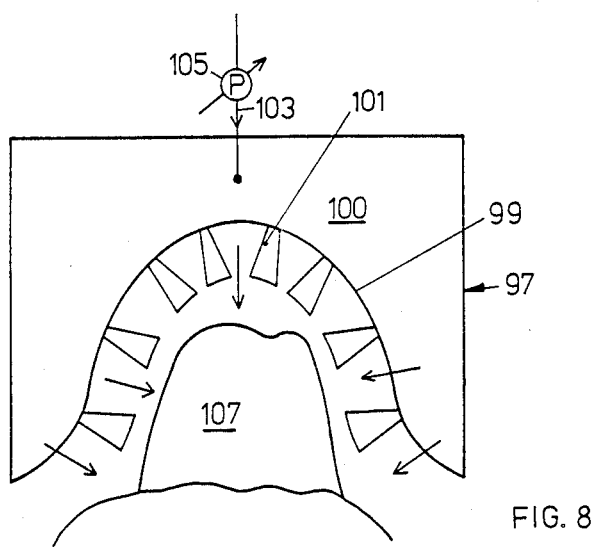
Figure 11A:
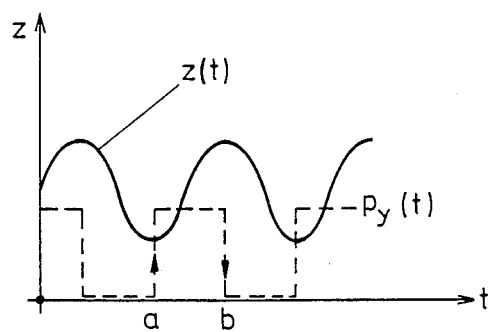
Figure 11B:
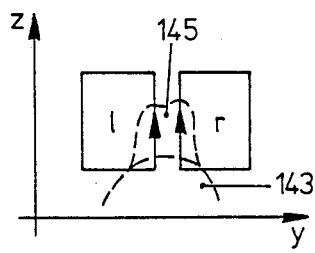
Figure 12:
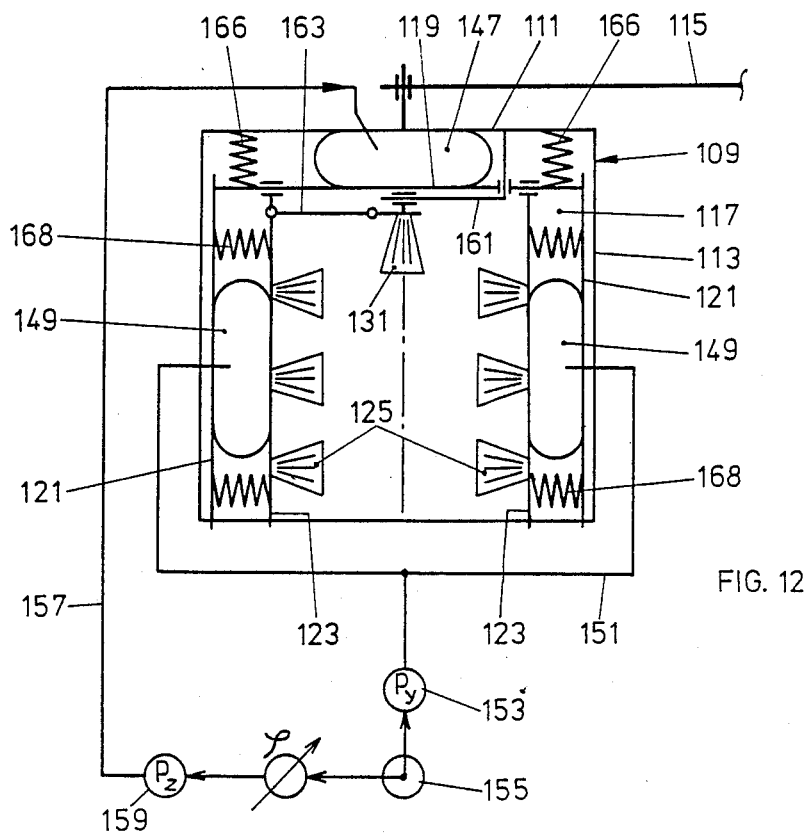
Figures 13A, 13B:
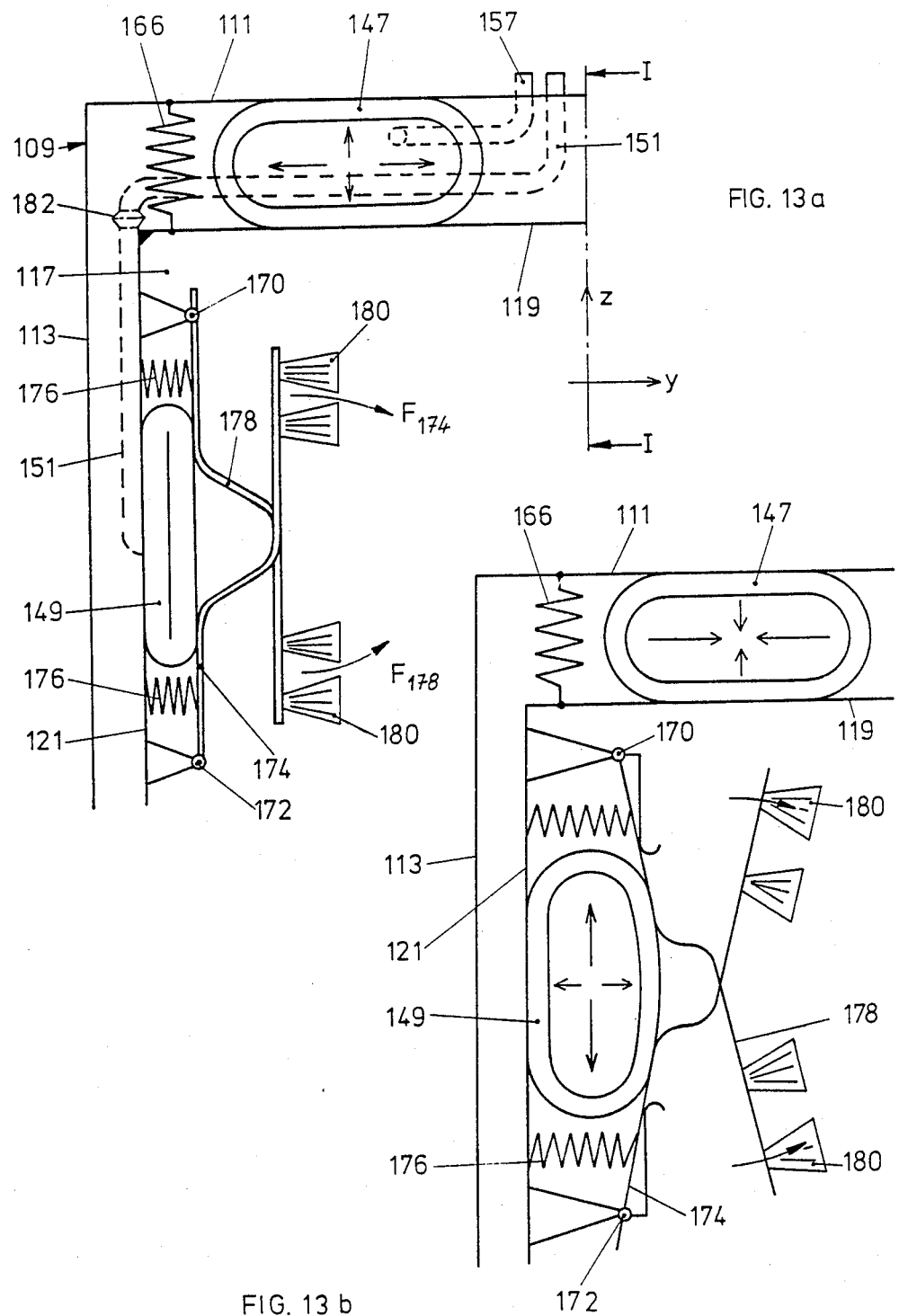
Figure 13C:
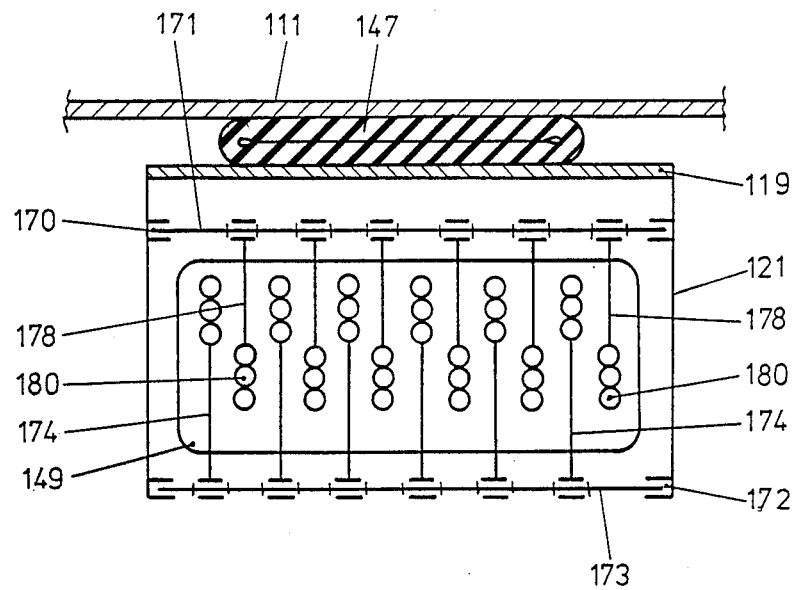
Figure 13D:
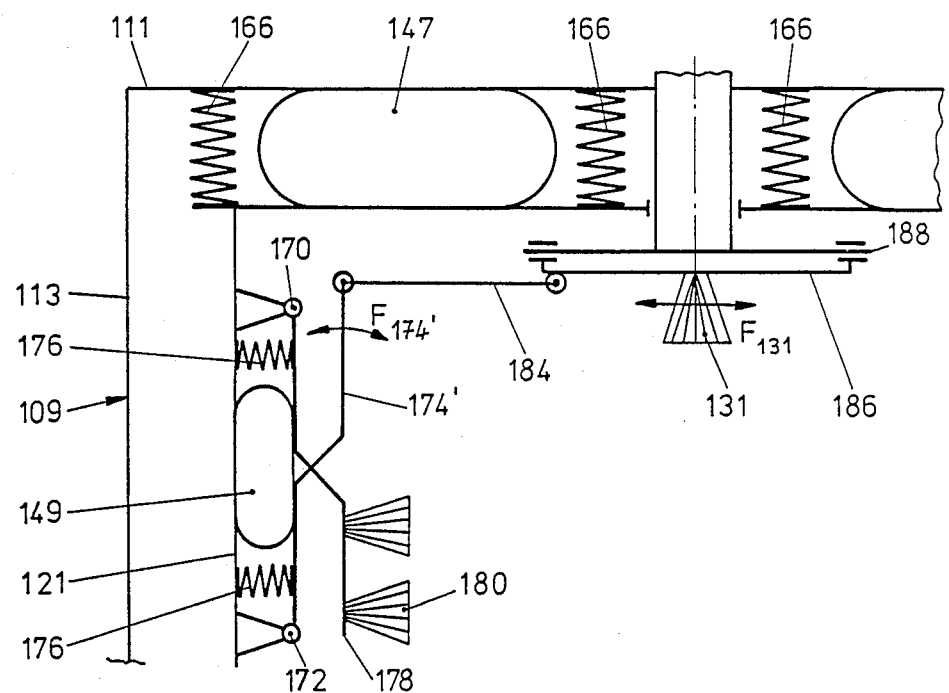
Figures 14A, 14B:
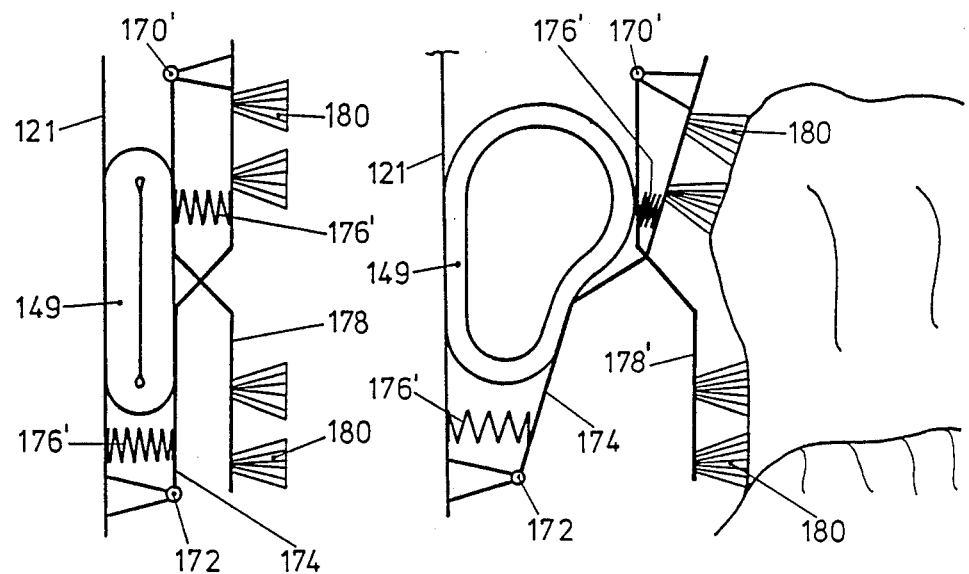
Figure 14C:
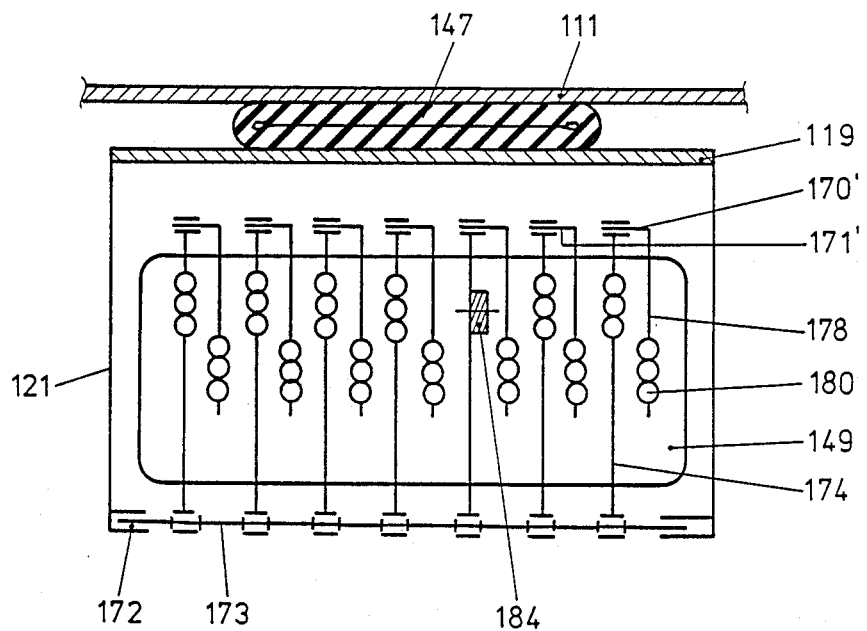
Figure 15:
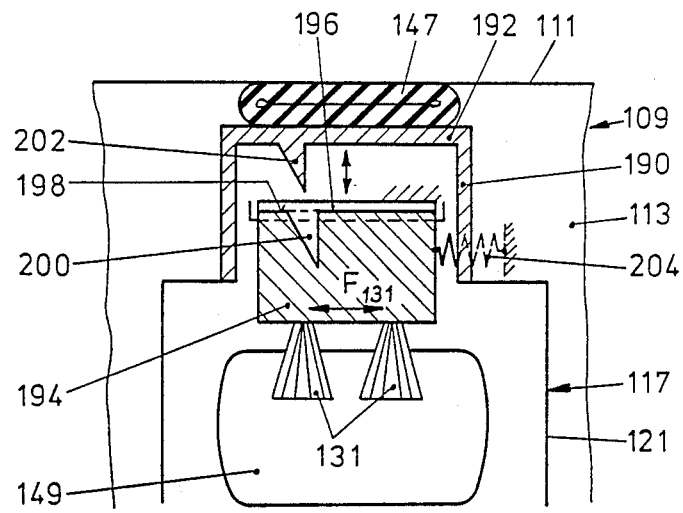
Figure 16:
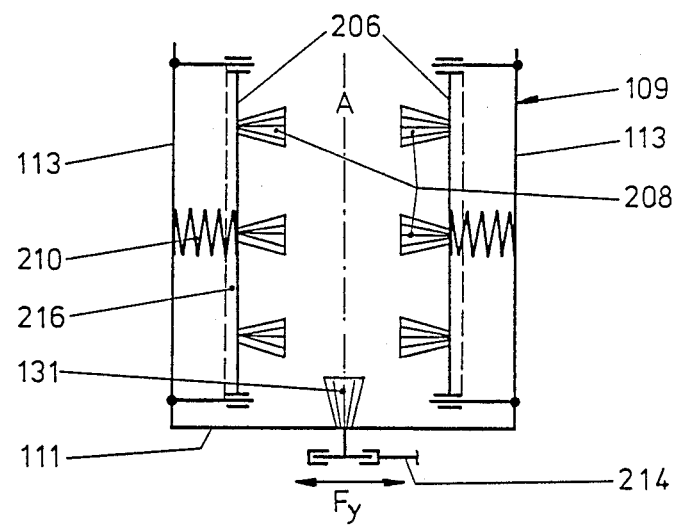
Figure 17:
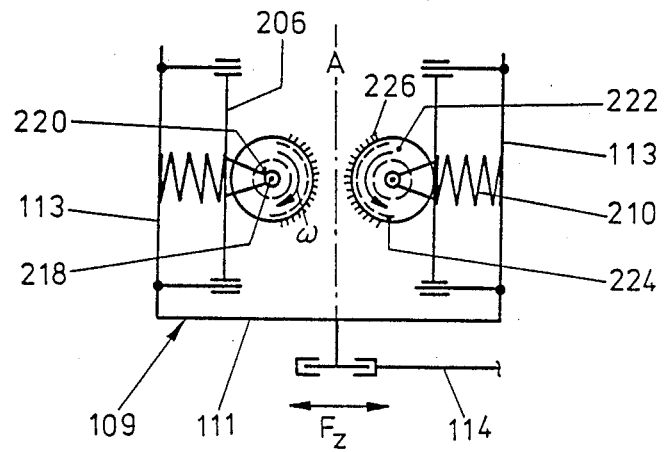
Figure 18:
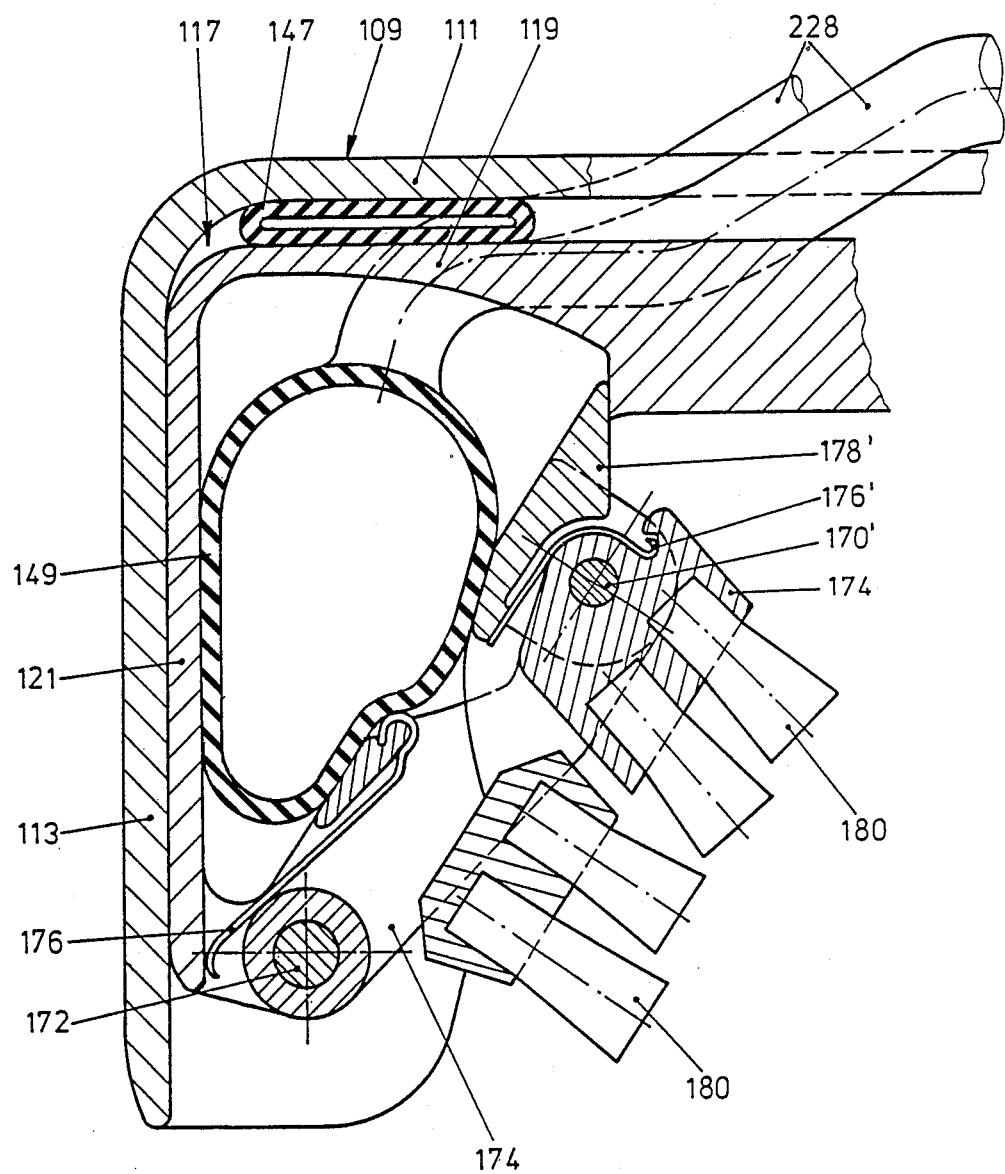
Figure 19:
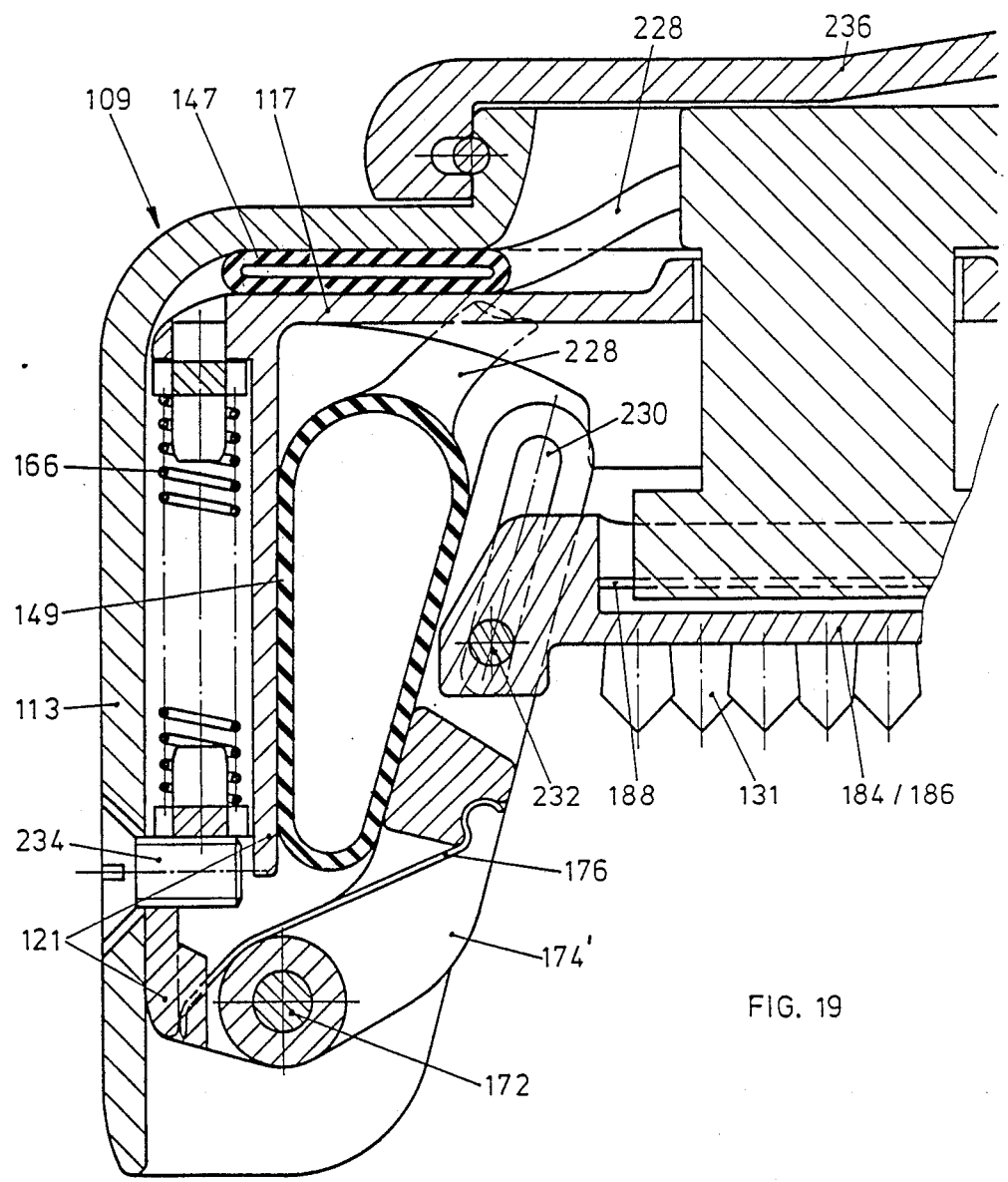
Figure 20A:
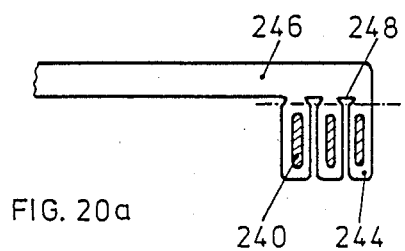
Figure 20B:
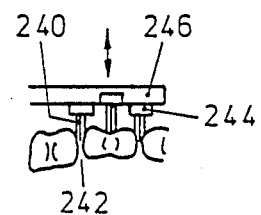

The invention will now be explained by way of examples with reference to drawings, in which FIGS. 1a–1c are three schematically drawn embodiments of a tooth cleaning device according to the invention for at least two-sided tooth cleaning, FIG. 2a is a principal illustration of the pressure control between cleaning elements and tooth on a tooth cleaning device according to the invention, FIG. 2b is a schematic illustration of an embodiment for the pressure control as per FIG. 2a with snap-action spring, FIG. 2c is a further schematic embodiment of the pressure control as per FIG. 2a with spring elements and stop, FIG. 3a shows, by way of a schematically drawn tooth with gum, the movement coordinate for the cleaning element movement on a tooth cleaning device according to the invention and the principal dependence from the cleaning pressure and movement in the movement coordinate, FIG. 3b is a schematic illustration of an embodiment of the cleaning element movement on a tooth cleaning device according to the invention, FIG. 4 is a schematic side view of a tooth cleaning device according to the invention in analogy to FIG. 1c, FIG. 5, in analogy to the illustration as per FIG. 4, is a further embodiment of a tooth cleaning device according to the invention, for ensuring at least approximately equal cleaning pressures between tooth and cleaning elements on the inner and outer faces of the tooth, FIG. 6 is an illustration analogous to FIG. 5 of a further embodiment of a tooth cleaning device according to the invention, with resetting, rubber-elastic skins, FIG. 7 is a schematic side view of a further embodiment of a tooth cleaning device according to the invention with napped cleaning element carrier for automatic pressure adaptation between individual cleaning elements and a tooth, FIG. 8 is a schematic illustration of a further embodiment of the tooth cleaning device according to the invention with a single pressure chamber for multi-sided embracing of a tooth to be cleaned, FIG. 9 is a partial view of a napped cleaning element carrier in non-tensioned and in tensioned position, analogous to the carrier of FIG. 7, FIG. 10 is a schematic illustration of a preferred tooth cleaning device according to the invention for at least two-sided tooth cleaning, under at least approximately equal cleaning pressures and for performing a cleaning-optimal wiping movement with the cleaning elements, FIG. 11a shows, above the time axis, the qualitative progression of cleaning element movement and pressure application on a device as per FIG. 10, FIG. 11b shows, in the figure plane of FIG. 10, the principal movement of the left and right cleaning elements, FIG. 12 shows principally and schematically a preferred embodiment of a tooth cleaning device as per FIG. 10, FIG. 13a is an enlarged, schematic partial view of a device according to the invention, principally as per FIG. 12, with rocker arm actuation of the cleaning elements, FIG. 13b is the arrangement as per FIG. 13a, with swung-out rocker arms, FIG. 13c is a schematic view, partially sectioned, along line I—I of FIG. 13a, FIG. 13d is an illustration analogous to FIG. 13b, with a principal drive of tooth top-surface cleaning elements, FIG. 14a is a partial view analogous to the view of FIG. 13a, with a further variant of the rocker arm arrangement, FIG. 14b is the arrangement as per FIG. 14a with swung-out rocker arms, FIG. 14c is a view analogous to that of FIG. 13c, of the arrangement as per FIGS. 14a and 14b, FIG. 15 is a schematic longitudinal section as per axis A of FIG. 12 through a device according to the invention, with a further variant of drive elements for tooth top-face cleaning elements, FIG. 16 is a schematic view analogous to FIG. 12 of a further embodiment of the tooth cleaning device according to the invention, FIG. 17 is a view analogous to FIG. 16 of a further embodiment of the cleaning device according to the invention, FIG. 18 is a longitudinal section of one side of a tooth cleaning device in the preferred form of embodiment analogous to the schematic illustration in FIGS. 14a and 14b, with swung-out rocker arms, FIG. 19 is an illustration analogous to FIG. 18, but without the rocker arms with cleaning elements, showing a preferred drive of tooth top-face cleaning elements, FIG. 20a is a schematic side view of a further, simple device according to the invention, FIG. 20b shows schematically the action of the device as per FIG. 20a, FIGS. 21a, b are two schematic views of a further embodiment of the device.

According to FIGS. 1a–1c a tooth cleaning element according to the invention for simultaneous cleaning of at least two tooth surfaces comprises a guiding grip or hand grip, on which is provided, preferably movably, shown rotatably in a bearing 3, a frame 5 or 5a. The frame is, as shown at 5, shaped in principle either in the form of an "L" or as shown at 5a, in the form of a "U". With this arrangement the concave side of the L, like that of the U, is facing away from the hand grip enabling the frame 5 or 5a to be placed over a tooth 7 of a set of teeth. By means of the hand grip 1 the device is then moved along the row of teeth. Tufts of bristles 9 are provided as cleaning elements in the embodiment according to FIG. 1a on both sides of the L. According to the embodiment of FIG. 1b both sides of the L are covered without interruption with cleaning elements 11 resembling a continuous carpet of bristles. As shown in a broken line in FIG. 1b frame 5 may also be equipped with a covering of cleaning elements 11 or 9 on three sides. FIG. 1c is a schematic illustration of the preferred embodiment in this regard, i.e. with respect to two-sided tooth cleaning, with sub-frame 5a, on which are provided, at least on the sides of the U, tooth cleaning elements in the form of tufts of bristles analogous to the tufts 9 in FIG. 1a or in the form of continuous cleaning elements 11 resembling carpet sections of bristles.

The arrangement illustrated in principle in FIGS. 1a–1c makes the cleaning of teeth substantially easier for the user in that it is possible, in particular with the embodiment as per FIG. 1c with possibly additional cleaning elements arranged at the base of the U for cleaning the top of the teeth, to place the cleaning device over a tooth and to guide it by means of handgrip 1 along the teeth while cleaning their inner and outer faces.

As already mentioned, a further requirement part of the invention is to be seen in the aim of controlling the cleaning pressure between the cleaning elements and the tooth. If excessive pressure is applied, there is the danger, in particular in the area of the neck of the tooth, that the gum is damaged by rough mechanical treatment and the tooth enamel is impaired. If, on the other hand, not enough cleaning pressure is applied, good cleaning of the tooth is not ensured. As shown in FIG. 2a, a cleaning device meeting this requirement part, comprises a reference system such as a hand grip 12, in relation to which a cleaning element carrier 14 is movably, in particular movably in a linear direction, mounted, whereby a pressure-registering arrangement, shown schematically at 16, is active between the reference system 12 and the cleaning element carrier 14 and is preferably combined with at least one pressure-limiting arrangement or one maximum-pressure-indicating arrangement 18, which either limits the pressure to a maximum or at least indicates to the operator, when admissible pressure is reached or exceeded. With this arrangement it is naturally understood that pressure registration, as with the pressure measuring arrangement 16, is effected preferably by registering the displacement path of the cleaning element carrier 14 with reference to the reference system 12, such as against the force of a spring, and that pressure limiting, as shown schematically with the limiting arrangement 18, may be effected by a stop between reference system and cleaning element carrier or by alerting the operator audibly and/or sensibly, as soon as admissible pressure has been reached. In FIG. 2b, showing a realistic embodiment of the principle as per FIG. 2a, the cleaning elements, whether in the form of tufts of bristles or a carpet of bristles 11, are arranged on a snap-action spring 20, which is mounted to a hand grip 22 via mounting brackets 24 for instance. The cleaning elements are brought into contact with the tooth, no matter on which side of the tooth, for instance with the top of the tooth as shown. When pressure is applied to the cleaning elements 11 the snap-action spring 20 will initially deflect sideways within the scope of its own elasticity and that of the mounting brackets 24. If, however, treatment or cleaning pressure exceeds the pre-set amount, the snap-action spring 20 will snap back into the position drawn as a broken line in order to return into its original position when pressure is relieved. This snapping effect is audible and/or will be felt on the hand grip 22. The snap-action spring 20 thus acts as a maximum-pressure-indicator with simultaneous pressure limitation being achieved through the withdrawing of the cleaning elements. With the embodiment as per FIG. 2c indication of maximum cleaning pressure is realized in that a stop 32 is arranged between hand grip 26 and a cleaning element carrier 28 with the cleaning element carrier 28 being elastically supported against a hand grip 26. When a pressure corresponding to the spring constants and the stop dimension is reached, carrier 28 contacts stop 32 which is felt on the hand grip 26. With this arrangement the stop 32 may be designed as a regulating screw, with which admissible cleaning pressure may be individually set.

With the embodiments shown in principle in FIG. 2 cleaning pressure is thus controlled in the sense that it is either limited as in the arrangement as per FIG. 2b, and/or indicated to the user when the pre-set maximum value is reached, thereby meeting, in principle, the second, intrinsically independent part of the requirement of the invention, which is to control cleaning pressure on a cleaning device. Further embodiments which will be described, also demonstrate the possibility of pre-setting the cleaning pressure.

The third part of the requirement consists in achieving that the tooth is cleaned from the gum 34 towards the crown of the tooth in +z-direction at cleaning contact pressure, in −z-direction, on the other hand, under reduced, or if possible zero bearing pressure between cleaning elements and the tooth/gum. Thus, as also illustrated in FIG. 3a, bearing pressure $p_R$ is built up in a lower position, corresponding to $z_o$, with the tooth cleaning elements being advanced, at this pre-set cleaning pressure, in the +z-direction against the tooth 36. When the upper position, e.g. corresponding to $z_1$, is reached, cleaning pressure is reduced, and the cleaning elements are returned in −z-direction into the position corresponding to $z_o$. This may also be achieved, as schematically shown, for example, in FIG. 3b, by a rotating tooth cleaning element 38 in the form of a cylindrical or conical brush 38, which is made to rotate about an axis $A_{38}$ with a direction of rotation $\omega$, such that in the contact area between brush 38 and tooth 36, the required movement from the gum towards the tooth is achieved.

FIG. 4, in analogy to FIG. 1c, shows a simple embodiment of the tooth cleaning device according to the invention. It comprises a U-shaped carrier frame 41 with sides 43 and base 45. Cleaning elements, such as tufts of bristles 47, on both sides 43 protrude against the axis of symmetry A of the U-shaped carrier frame 41. Base 45 is movably, at least pivotably about one axis parallel to axis A, attached to a guiding grip 50, such a hand grip. Base 45 may be provided with further cleaning elements such as tufts of bristles 49.

The schematically illustrated, highly simple device is placed over the teeth with the U-carrier frame opening, the carrier frame 41 with its tufts of bristles 47, possibly 49, being guided over the teeth by means of handle 50, whilst automatically adapting to the tooth position, for instance by pivoting in bearing 51. This allows two-sided cleaning of the teeth, without requiring cumbersome movements being performed such as is the case with conventional tooth brushes when cleaning the inner face of the teeth.

FIG. 5 again, is a schematic illustration of a further development of the device as per FIG. 4, such, that at least approximately equal bearing pressures are achieved between cleaning elements and tooth on both sides of the teeth or on all envisaged cleaning contact areas. On sides 53 of carrier frame 52, shaped again as a U with 55 as the base, pressure generating elements are provided such as in the form of pressure bubbles 57. Cleaning elements, such as tufts of bristles 59, are riding on the bubbles 57; they face the axis of symmetry A of the U. The two bubbles 57 provided on sides 53 are in communication with each other via a line 61 and are preferably linked to a pressure supply not shown via an adjustable pressure setting valve 63. A liquid or gaseous medium, preferably air, is used as pressure medium. The carrier frame 52 is pivotably mounted on a guiding grip 65 with reference to the axis A, with pressure being supplied via the illustrated line system 64, preferably through the guiding grip 65.

FIG. 6 shows a tooth cleaning device designed in principle as that shown in FIG. 5, with the additional feature that the tufts of bristles 59 are not directly arranged on the pressure bubbles 57, but that a rubber-elastic skin 67 is provided on each side 53 which stretches over the respective pressure bubbles 57. The tufts of bristles 59 ride on the skin 67. The skins 67 make it easier, on the one hand, to attach the tufts of bristles 59, and on the other hand, have a pre-tensioning effect upon pressure bubbles 57. This allows higher pressures to be used on the supply side, with the associated skins 67 absorbing part of the internal pressure of the bubbles 57, leaving only the differential pressure to act as cleaning pressure upon the tooth. In addition the skins 67 have a resetting effect upon the bubbles 57.

With the embodiments of the tooth cleaning device, shown in FIGS. 5 and 6, it is ensured that at least approximately equal contacting pressures are guaranteed everywhere between the provided cleaning elements and the tooth. In addition the tufts of bristles set themselves individually against the tooth, engage into inaccessible gaps and grooves such as the interdental gap. The pressure to be maintained can be set with the aid of the pressure regulating valve 63, in the sense that pressure is set and limited.

The bearing between carrier frame and guiding grip may be a swivel bearing such as shown in the figures, but may also be a bearing which allows pivotal movement about two or even three spatial axes.

FIG. 7 shows a schematic illustration of a further tooth cleaning device, on which a maximum cleaning pressure is guaranteed to be maintained locally. On a U-shaped carrier frame 69 with sides 71 and a base 73, the latter pivotably mounted on a guiding grip 75, a rubber-elastic nap structure 77 has been inserted, which forms a concave arch 79. The nap structure 77 comprises totally enclosed, for instance truncated-cone-shaped, radially projecting shapings 81 which are surrounded with regard to the arch 79, by snap areas 83, snapping radially inward. A tuft of bristles 85 rides on each of the shapings 81. The nap structure 77 is supported against a sieve-like underlay 87, for instance wire netting, whereby the shapings 81 are preferably aligned with the mesh central axes as illustrated at B, and the snap areas are correspondingly aligned with the bars or wires of the sieve. When pressure is applied to the tufts of bristles 85, the shapings 81 together with the snap areas surrounding them, will initially individually elastically absorb the cleaning pressure. If, however, the cleaning pressure exceeds the pre-set value, the shapings 81 will snap radially inward, as shown in broken line and snap out again when pressure is relieved, as is known, for instance, from rubber-elastic key fields. In this way it is ensured that bearing pressure or cleaning pressure remains limited individually at each of the provided tufts of bristles 85.

With regard to the function of the nap structure 77 in FIG. 7 reference should be made to the schematic illustrations of FIG. 9. These show, in the form of cutouts, the sieve-type carrier structure 87 and the napped rubber-elastic structure 77 with tufts of bristles 85 attached to it. Shown above it is a schematic drawing of the tooth marked 89. Deviating from the illustration in FIG. 7 and as an alternative, the nap structure 77 is provided with snap-in concave disc areas 93 which are surrounded by burr areas 95 preferably also circular in shape. Stop areas 91 protruding towards the tooth 89 ride on the burr areas, while the tufts of bristles 85 are arranged at an oblique angle on the disc areas. As tooth 89 is brought into contact with the tufts of bristles 89 and pressure is raised, tooth 89 will eventually contact the stop areas 91 pushing down on the nap structure 77 and causing it to 'snap inward'. As a result, the tufts of bristles 85 are moved tiltingly back and forth causing a reciprocal brushing movement by the individual tufts of bristles 85 on the tooth 89. Analogous to FIG. 7 the side of the U-shaped carrier frame 69 is marked 69.

FIG. 8 shows a schematic illustration of a further embodiment which is based on those in FIG. 5 or 6. Here a carrier frame 97, again U-shaped, is movably, preferably pivotably mounted on the guiding grip not shown. The inner space of the U formed by the carrier frame 97 is covered with a rubber-elastic skin 99 thus forming a closed chamber 100. Again a pressure-setting valve 105 is preferably provided by means of which pressure in the chamber 100 may be limited or set. After placing carrier frame 97 over the tooth schematically drawn as 107, pressure is built-up in the chamber 100, so that the tufts of bristles 101, all at the same pressure, contact the surface of the tooth. In this way it is ensured that cleaning contact pressure between the individual tufts 101 and the tooth 107 is at least approximately equal all over.

Figure 3B:
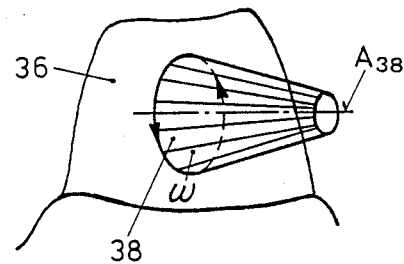

As has already been mentioned, a tooth cleaning device shall meet yet a further requirement in addition to those already mentioned; this concerns the cleaning of the tooth by a wiping movement from the gum to the tooth. Such a movement has already been discussed in connection with FIG. 3. A further realistic embodiment of this principle, and one to be preferred, shall now be discussed with reference to the schematic illustration of FIG. 10. Again a U-shaped carrier frame 109 is provided incorporating a base 111 and sides 113. Carrier frame 109 is rotatably mounted on a guiding grip 115, as already described. A cleaning frame 117 is linearly movably mounted in piston-type fashion in the carrier frame 109, this cleaning frame consisting of a base 119 linearly movable in z-direction between the sides 113 and two cleaning frame sides 121 sliding along the sides 113. A cleaning element carrier 123 is provided on either side which is linearly movable in y-direction.

From this follows that the base 119 is movable only in z-direction with reference to the carrier frame 109, while the cleaning element carriers 123 are movable both in z- and in y-direction, with reference to the frame 109. Both cleaning element carriers 123 carry inwardly protruding cleaning elements such as tufts of bristles 125. A driving element 127 acts between base 111 as reference base and base 119, and pressure generating elements 129 act between sides 121 and cleaning element carriers 123. Also provided, and shown schematically, are top-surface cleaning elements such as top-surface bristle tufts 131 which, independent from the movement of the cleaning frame 117, as shown, are linearly movable in x-direction for instance, having been provided with appropriate drive elements 133. A preferred embodiment of said drive elements and pressure-generating elements will not be discussed in any detail. As shown by way of a cutout to the right of FIG. 10 it is perfectly feasible, instead of using linearly movable cleaning element carriers 123, to employ rocker arms 137 as cleaning element carriers supported like rocking levers in bearings 135, which are provided with cleaning elements such as bristle tufts 139. Again pressure-generating elements 141 act between sides 121 of the cleaning frame 117 and rocker arms 137. Instead of a linear movement in y-direction, as per embodiment to the left of FIG. 10, the embodiment on the right provides for a pincer-type tilting movement of the bristle tufts 139 with one component in z-direction and one component in y-direction.

The now following description relates to the controlling of the pressure-generating elements 129 and drive element 127, by which is achieved a wiping two-sided cleaning of the teeth from the gum towards the crown of the tooth at preferably equal pressures controlled on both sides. In FIG. 11 the required movement of base 119 in FIG. 10, marked z(t) has been qualitatively plotted above the time axis with pressure control for the pressure generating elements 129 being shown as a broken line marked $p_y(t)$. When base 119, according to FIG. 10, is in the lowermost position, i.e. as far as possible over the gum during use, pressure is raised as shown at a, so that during subsequent lifting of base 119 and thus the cleaning elements 125, the latter glide along gum and tooth with optimal cleaning pressure applied by the pressure-generating elements 129. When base 119 has reached its uppermost position, i.e. is furthest from the gum, pressure is reduced, as per b in FIG. 11a, preferably to zero, so that the cleaning elements 125 lift as far as possible away from the tooth or at least rest against it with practically zero pressure. Now base 119 is returned into its starting position, where due to a renewed increase in pressure, the cleaning elements 125 are again placed against the gum. This shows that the movement in longitudinal direction of the tooth, marked z(t) has a lead over the pressure function $p_y(t)$ of $\Pi/2$. The illustrated synchronous progressions of pressure p(t) across the tooth and movement z(t) along the tooth lead to movement cycles, as plotted in FIG. 11b, for both lateral cleaning element carriers 123 with bristle tufts 125, whereby, in order to clarify their relation with the tooth in said figure, gum and tooth have been indicated as broken lines with 143 and 145 respectively.

In this way the already mentioned optimal wiping movement of the cleaning elements from the gum towards the crown of the tooth, i.e. from red to white, can be realized. FIG. 12 shows, again in schematic form and based on FIG. 10, a first principal step towards realization, in particular as regards the drive and pressure-generating elements 127 and 129 respectively of above mentioned figure. Corresponding components are marked with the reference numbers introduced in FIG. 10. As drive element marked 127 in FIG. 10 is provided a pressure bubble arrangement 147, which acts between base 111 of carrier frame 109 and base 119 of cleaning frame 117. As pressure-generating elements marked 129 in FIG. 10 are provided pressure bubbles 149 respectively on both sides between sides 121 of cleaning frame 117 and cleaning element carriers 123, whereby the latter communicate preferably via a pressure line 151 and are linked to a pressure supply 153, driven from a motor 155, for example. The bubble arrangement 147 acting as drive element is, in turn, linked to a pressure supply 159 via a pressure line 157. Pressure supply 159 is preferably pulsatingly driven from the same motor 155, but shifted by one phase $\Psi$ preferably on the mechanical side.

In difference to the illustration in FIG. 10 the top surface bristle tufts 131 in this figure are linearly movable in y-direction, which is realized in that these tufts are movably mounted in a linear guide 161 with reference to the carrier frame 109, with their y-movement being controlled by transferring the movement of one of the cleaning elements 123, such as by a transfer lever 163. This provides a simple method for realizing the drive of the top surface bristle tufts 131.

Pre-tensioning and return spring elements 166 act between base 111 and base 119, and analogously, spring elements 168 act between sides 121 and cleaning element carriers 123. These spring elements pre-tension, on the one hand, pressure bubbles 147 and 149 resulting in higher supply pressure for operating and on the other hand, ensure a rapid withdrawal of the cleaning elements both in z- and in y-direction when the pressure drops, which is important, in particular with pulsating pressure control.

FIG. 13a shows a further preferred embodiment of the arrangement as per FIG. 12, as a further development. Again parts which correspond to those in FIG. 10 or 12, have been marked with the same reference numbers. The cleaning element carriers are shaped as rocker arms, analogous to the variant on the right of FIG. 10. On the sides 121 of cleaning frame 117, at the far end and near the base, swivel bearings 170 and 172 are provided. At the far-end-bearing 172 a rocker arm arrangement 174 is pivotably mounted against the force of a spring 176. Analogously at the swivel bearing 170 a rocker arm arrangement 178 is pivotably mounted against the force of a further spring 176. The rocker arm arrangements 174 and 178 are both terminally mounted at their respective bearings and at their other end, carry cleaning elements such as tufts of bristles 180. Between the rocker arm arrangements 174 and 178 and the respective sides 121 is again provided at least one bubble 149. Analogous to FIG. 12 the bubbles 149 on both sides are lined to a pressure supply not shown via a pressure line 151 shown as a broken line and one or several flexible couplings 182. The drive of base 119 is effected in the described manner via bubble 147 acted upon by at least one pressure line 157. Due to the pressure acting upon bubbles 149 the rocker arms 174 and 178 are swung in the directions indicated with $F_{174}$ and $F_{178}$ in the figure, with one component in y-direction. The position of the rocker arms with their associated cleaning elements, for an at least partially pressurized bubble 149, is shown in FIG. 13b. The arrows drawn inside the bubbles 147 and 149 have been provided to indicate the associated pressure change tendencies in the position shown: When bubble 149 is under increasing pressure, bubble 147 is relieved, in order to move in the already described manner from the gum to the tooth. FIG. 13c shows a partial view of the arrangement as per FIG. 13a when viewed in the direction of line I—I. In particular the design shapes of rocker arms 174 and 178 are revealed. Swivel axes 171 and 173 extend as bearings 170 and 172 along the sides 121 with two or more comb-like staggered, meshing rocker arms 174 and 178 arranged on them with bristle tufts 180 mounted on one end. By providing a plurality of comb-like meshing rocker arms, respectively reciprocating with the pressure bubble 149 associated with the side 121, optimal contact of cleaning elements even on irregular tooth surfaces, such as in the interdental gap, is ensured.

FIG. 13d shows the arrangement as per FIG. 13a with the addition of the schematically drawn drive of top surface bristle tufts 131. On one of the provided rocker arms 174', arranged analogously but preferably not carrying any bristle tufts 180, a transfer lever 184 is pivotably mounted. The top surface bristle tufts 131 travel on a slide 186, linearly guided on a corresponding guide 188, on carrier frame 109. The transfer lever 184 is e.g. also pivotally linked with the slide 186, such that for an oscillating swivel movement as per $F_{174}$, of rocker arm 174', due to the effect from pressure bubble 149, a back-and-forth pendulum movement, marked $F_{131}$, of the top surface bristle tufts 131 in the direction as per spatial axis y of FIG. 10 results. In this way, without providing additional drive elements, a pressure-actuating element corresponding to pressure bubble 149, is simultaneously realized as drive element for the said top surface bristle tufts 131.

FIGS. 14a–14c show a further embodiment of the rocker arm mounting in partial views analogous to illustrations 13a–13c. Again the same reference numbers have been used. Instead of providing a swivel bearing 170 for the rocker arms 178 mounted towards the base 119, such as revealed in particular in FIG. 13c, each of the arms 174 terminally mounted on axis 174 with reference to the sides 121 carries a swivel bearing 171' on that end on which it is also fitted with bristle tufts 180, with rocker arms 178' mounted to the swivel bearing 171' analogous to rocker arms 178 in FIG. 13. Thus in contrast to the illustrations of FIG. 13, the rocker arms in the embodiment as per FIGS. 14 are terminally mounted one on the other. Again a transfer lever as in FIG. 13c, here marked 184, is preferably provided for the drive of top surface bristle tufts such as 131 in FIG. 13d.

FIG. 14b shows, how in this preferred mounting variant of the rocker arms the provided bristle tufts 180 qualitatively contact a tooth or the gum. With this embodiment the pre-tensioning or return spring for the rocker arms 178' is preferably provided between rocker arms 174 and 178', as marked in particular with 176' in FIG. 14a.

FIG. 15 shows a further drive possibility for the top suface bristle tufts 131, here as a schematic illustration viewed analogously to FIG. 13c or 14c, wherein for better clarity however, the rocker arm arrangement has been omitted. The latter are arranged as already explained. The bubble 147 resting on the base 111 of carrier frame 109 acts in the already described manner upon cleaning frame 117 with its sides 121, as drive in z-direction. In the central area, cleaning frame 117 has a shaping 190 extended towards the base 111 of carrier frame 109, and this is in the form of a trough open at both ends on the sides 113 of carrier frame 109 and facing base 111, with a trough base 192 supported against bubble 147. This shaping 190 defines a trough open from one carrier frame side 113 to the other and extending parallel to base 111. A slide 194, movable in the direction marked y in FIG. 10, is supported on guides 196 against these sides 113 of carrier frame 109. Side 198 of slide 194 facing trough base 192 has a key-guide recess 200, whilst base 192 carries a key-drive shaping 202 cooperating with the key guide recess 200. When cleaning frame 117 is lifted due to pressurizing bubble 147, key drive shaping 202 connects with key guide recess 200, and slide 194 is moved to the left as per FIG. 15. As bubble 147 is depressurized, slide 194 is returned due to the action of a spring 204, which latter is mounted to the slide 194 on the one hand and to the carrier frame 109 on the other. This causes the reciprocal movement $F_{131}$ of the surface bristle tufts 131.

FIGS. 16 and 17 again are schematic illustrations of two further embodiments of the tooth cleaning device according to the invention. Up to now the pressure-generating elements have been illustrated mainly as being pneumatically, or hydraulically actuated bubbles. FIG. 16, however, shows an embodiment, where the pressure-generating elements have been shaped differently. On sides 113 of the carrier frame 109 the cleaning element carriers 206 are mounted linearly movably and vertically to axis A of the carrier-frame U.

They carry respectively one or several bristle tufts 208. Compression spring elements 210 are arranged between the sides 113 of carrier frame 109 and cleaning element carriers 206 and these drive the cleaning element carriers 206 against axis A.

One or several top surface bristle tufts 131 on the base may be, as has already been described and has therefore been indicated schematically only, provided so as to be movable or non-movable. Carrier frame 109 is movably mounted on a guiding grip 214, but in this embodiment is preferably swingable not only with reference to axis A, but also linearly movable in the direction of guiding grip 214. This linear movability extends therefore in y-direction as per FIG. 10 and is marked $F_y$.

By placing the arrangement as per FIG. 16 over a tooth to be cleaned, the two cleaning element carriers 206 automatically adjust against the force from the spring 210 such that the reaction forces created on both sides of the tooth are in equilibrium, which presupposes that the mentioned y-movability of the carrier frame 109 is ensured. If this equilibrium of forces shall also correspond at least approximately, to a uniform distribution of pressure, a rubber-elastic intermediate carrier 216 is preferably provided, as indicated by a broken line, on which the bristle tufts 208 are arranged, in order to enable the latter to adapt flexibly and individually to the respective tooth surface areas to be cleaned. The arrangement illustrated in FIG. 16 thus also ensures, in particular in conjunction with the rubber-elastic intermediate carriers 216, an at least approximately uniform distribution of pressure on both sides between cleaning elements and tooth surfaces to be cleaned.

FIG. 17 shows a further embodiment of the tooth cleaning device according to the invention, which incorporates the recognisedly optimal massaging movement from the gum towards the crown of the tooth. Although the feature of optimal cleaning movement is realizable without the assurance of at least approximately equal cleaning pressures on both sides, FIG. 17 shows an arrangement, where apart from the said optimal movement a uniform distribution of pressure is also ensured to a certain extent. To achieve this, the arrangement has been shaped analogously to that in FIG. 16 including cleaning element carriers 206 and compression spring arrangements 210. It is of course understood that the pressure generating elements may also be in the form of other elements such as the earlier described pressure bubble arrangements for instance. On the cleaning element carriers 206 rotary drive elements such as small size water or air motors 220 with axes 218 extending across base 111 are provided which drive cleaning rollers 222. Preferably the cleaning rollers 222 extend in the direction marked x in FIG. 10 and have a rubber-elastic carrier covering 224 to which cleaning elements such as schematically drawn bristles 226 are attached. The small size motors 220 are driven in the direction marked ω, thus establishing the optimal wiping movement from the gum to the crown of the tooth. It is of course understood that a further simplified tooth cleaning device according to the invention, with reference to the axis of symmetry A of the arrangement as per FIG. 17, may comprise only one half. In this case the carrier frame would be L-shaped with only one small size motor/cleaning roller arrangement. The desired movement may also be realized—without motor drive—by direction-specific damping such a ratchet system. Then the tooth is pushed in between the freewheeling rollers and withdrawn against a roller rotating restraint.

FIG. 18 shows a preferred realizable form of the cleaning device according to the invention in part longitudinal section —analogous to the illustration of FIG. 13a for example—laid out, in principle, as per FIGS. 14a–c. Correspondingly the same reference numbers have been chosen. In addition the running of the pressure lines 228 to bubbles 149 and 147 is revealed. The pre-tensioning and return springs 176 and 176' of FIG. 14 are shaped as leaf springs acting, on the one hand, between sides 121 of cleaning frame 117 and rocker arms 147 and, on the other hand, between the last mentioned rocker arms 147 and the levers 176 mounted on bearings 170'.

FIG. 19 shows, in central longitudinal section through the device as per FIG. 18, the drive of the top surface bristle tufts 131. This drive corresponds to that described in principle in FIG. 13d. As can be seen, a rocker arm 174' is provided which is equipped with a guiding groove 230 in its end, in which a bolt 232 is slidingly guided. The bolt 232, in turn, is mounted to slide 186 which therefore simultaneously serves as transfer lever 184. A pre-tensioning and return leaf spring 176 is provided analogously to spring 176 as per FIG. 18 for the rocker arms 174 carrying the bristle tufts. The compression springs 166 rest, on the one hand, against a stop bolt 234 firmly connected to the sides 113 of carrier frame 109, and the other hand, against cleaning frame 117. The figure further reveals the arrangement of the guiding grip 236 with the pressure lines 228 running inside it for separate pulsating control of the drive elements such as bubbles 147 and the pressure generating elements such as bubbles 149.

FIGS. 20a and 20b show a schematically drawn further embodiment of the device according to the invention, on which cleaning elements such as elongated bristle tufts 240 mold themselves in a simple way individually into inaccessible parts of the teeth such as the interdental gap 242. To this end they are attached to lever arrangements 244 which, in turn, are spring mounted on a guiding grip 246. The grip 246 and the levers 244 may be manufactured from the same material, and contrictions 248 for forming a springy, lever-specific swivel connection may be provided. It is also possible for the levers 244 to be supported against leaf springs.

Figures 21A, 21B:
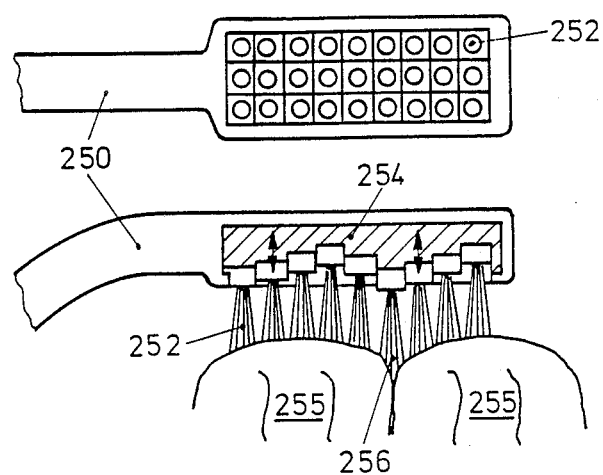

In the embodiment as per FIGS. 21a, 21b, bristle tufts 252 are spring mounted individually in their axis such as on a spring pad or on individual spring elements, on a guiding grip 250. This embodiment, too, allows the teeth to be cleaned well, even in areas which are difficult to access such as the interdental gap shown schematically as 256 between teeth 255.

It is furthermore possible for the earlier described wiping movement from the gum towards the crown of the tooth to be inverted so that the cleaning elements move from the crown of the tooth towards the gum, when during a tooth treatment the treatment material shall, for example, be pushed into the gum base. To do this, the movement described above may be inverted on the device.

With the described tooth cleaning device in its various embodiments, optimal cleaning of teeth is possible according to latest scientific knowledge. Although the pressure generating elements and also the drive elements mentioned are, in the main, water or air-pressure-actuated, i.e. pneumatic or hydraulic bubbles or bellows, or even spring elements, it is of course understood that other means, such as mechanical, electrical or electro-mechanical drives, with eccentrics for example, may be used for the control in tooth longitudinal or cross direction. In particular, the embodiment detailed in FIGS. 18 and 19 is the one preferred at the moment. With this arrangement it remains to be mentioned that the extent of swivel of the carrier frame 109, with reference to the guiding grip 236, is preferably limited by stops in order to prevent damage to the pressure lines 228 from excessive turning. Pressure generation is preferably also effected by small size motors preferably integrated in the guiding grip 236 and preferably supplied from batteries or accumulators. This will result in a mains-independent tooth cleaning device which can be used anywhere.

I claim:

1. A tooth cleaning device with at least one cleaning means mounted to a base arrangement, the device comprising:
   a first driving means for automatically driving said cleaning means in an oscillating manner in a first direction; and
   a second driving means controllable independently from said first driving means, for driving said cleaning means in a second direction substantially perpendicular to said first direction whereby said first and second driving means form a composite drive adapted to drive the at least one cleaning means relative to a handle supporting said cleaning means.

2. A device according to claim 1, wherein said cleaning means comprises at least two parts for defining a cavity-like chamber for accommodating at least one tooth.

3. A device according to claim 2, comprising pressure controlling means interposed between said cleaning means and said base arrangement for influencing a contacting pressure between a cleaning area of said cleaning means and a tooth.

4. A device according to claim 3, wherein said cleaning means comprises cleaning areas which position themselves individually according to reaction forces from a tooth.

5. A device according to claim 1, further comprising pressure controlling means interposed between said cleaning means and said base arrangement for influencing a contacting pressure between a cleaning area of said cleaning means and a tooth.

6. A device according to claim 5, wherein said cleaning means comprises cleaning areas which position themselves individually according to reaction forces from a tooth.

7. A device according to claim 1, wherein said first direction lies in an axis extending from a gum area to a crown of the tooth, said second driving means generating a first pressure between a cleaning area of said cleaning means and a tooth when said first direction runs from said gum to said crown and generating a second pressure when said first direction runs from said crown to said gum.

8. A device according to claim 1, wherein said base arrangement comprises a U-shaped frame, said cleaning means being provided at least at inner of legs of said U-shaped frame.

9. A device according to claim 1, wherein said cleaning means are mounted on said base arrangement through pressure generating means.

10. A device according to claim 9, wherein said pressure generating means comprises a plastic bubble arrangement driven by one of air or water.

11. A device according to claim 10, further comprising pretensioning means including spring means coupled with said bubble arrangement for offsetting a pressure generated by said bubble arrangements by a pretensioning pressure value.

12. A device according to claim 4, wherein said pressure generating means forms a drive means for a further cleaning means provided at a base of said U-shaped frame.

13. A device according to claim 8, wherein between both of said legs of said U-shaped frame and repective cleaning means, a bubble arrangement is provided, each of two bubble arrangement communicating with each other to ensure equal cleaning pressures on both of said legs of said U-shaped frame.

14. A device according to claim 8, wherein said driving means drive said cleaning means within a plane of said U-shaped frame so that parts of said composite drive in a vicinity of and substantially parallel to a symmetrical axis of said U-shaped frame extend towards a base of said U-shaped frame.

15. A device according to claim 8, wherein said cleaning means are arranged through pressure generating means on said legs of said U-shaped frame, said first driving means driving said cleaning means in a direction of said legs, and wherein said second driving means and said first driving means respectively control pressure and movement cyclically with a predetermined phase shift with respect to each other.

16. A device according to claim 15, wherein said second driving means generates a higher pressure whenever said first driving means drives said cleaning means towards a base of said U-shaped frame and reduces said force whenever said first driving means drives said cleaning means from said base of said U-shaped frame.

17. A device according to claim 16, wherein said second driving means and said first driving means each comprise a bubble arrangement, and wherein said bubble arrangement is driven by at least one of water or air.

18. A device according to claim 8, wherein said cleaning means at said legs of said U-shaped frame are pivotably mounted on axles, and wherein said axles lie at least nearly perpendicular with respect to a plane defined by said U-shaped frame.

19. A device according to claim 18, wherein said cleaning means at said legs of said U-shaped frame are mounted on axles at a free end region of said legs, and further cleaning means are mounted on axles arranged at a base of said U-shaped frame.

20. A device according to claim 18, wherein said cleaning means are mounted on rocker arms respectively mounted on said axles.

21. A device according to claim 20, wherein said cleaning means are mounted towards one end of said rocker arms, said rocker arms being mounted on said axles at opposite end regions thereof.

22. A device according to claim 20, wherein pressure generating means are provided between said rocker arms and respective legs of said U-shaped frame, said pressure generating means including a plastic bubble arrangement.

23. A device according to claim 20, wherein said rocker arms are mounted to a free end region of said legs by said axles, and further rocker arms are mounted to said rocker arms at a base of said U-shaped frame by further axles.

24. A device according to claim 23, wherein said rocker arms and said further rocker arms are alternatingly mounted.

25. A device according to claim 24, wherein said further rocker arms are pivotably mounted at least in part to said rocker arms.

26. A device according to claim 18, further comprising spring means for biasing said cleaning means towards said legs.

27. A device according to claim 8, wherein said cleaning means at said legs are linked to said legs through a carrier arrangement movable along said legs.

28. A device according to claim 27, wherein said cleaning means at said legs of said U-shaped frame are pivotably mounted on axles to said carrier arrangement, and wherein said axles lie at least nearly perpendicular with respect to a plane defined by said U-shaped frame.

29. A device according to claim 27, wherein said driving means comprises a bubble arrangement disposed between a base portion of said U-shaped frame and said carrier arrangement movable along said legs.

30. A device according to claim 8, comprising a further cleaning means arranged at a base of said U-shaped frame for cleaning an upper side of the tooth.

31. A device according to claim 30, wherein said further cleaning means is coupled with a drive means so as to enable a movement thereof at least in one component linearly within a plane at least nearly perpendicular to a plane defined by a base and the legs of said U-shaped frame.

32. A device according to claim 1, wherein said base arrangement is movably mounted on a handle.

33. A device according to claim 1, wherein pressure limiting means are provided between said cleaning means and said base arrangement.

34. A device according to claim 1, wherein said cleaning means comprises at least one flexible carrier means.

35. A device according to claim 34, wherein said at least one flexible carrier means is a nap structure.

36. A method for cleaning teeth comprising the steps of:
applying at least one cleaning means to a tooth to be cleaned;
driving said cleaning means relative to said tooth to be cleaned;
generating a first drive for automatically oscillating substantially along a first axis extending substantially parallel to a longitudinal axis of the tooth;
generating a second drive for automatically oscillating substantially along a second axis perpendicular to said first axis, said first and second drive being controllable independent from each other;
superimposing said two oscillating drives along said first and second axis to form a predetermined composite resultant drive for the cleaning means; and
applying said composite drive to said cleaning means, whereby said composite drive is relative to a handle means supporting said at least one cleaning means.

37. The method according to claim 36, whereby cleaning is simultaneously performed on at least two sides of a tooth.

38. The method according to claim 37, further comprising the step of controlling a cleaning pressure of said cleaning means on at least one of said teeth.

39. The method according to claim 38, wherein said cleaning means is moved along a direction from the gum toward the crown of said tooth when said cleaning means is nearer to said longitudinal axis of the tooth.

40. The method according to claim 37, wherein said cleaning means is moved along a direction from the gum toward the crown of said tooth when said cleaning means is nearer to said longitudinal axis of the tooth.

41. The method according to claim 36, whereby cleaning is performed with cleaning areas of said cleaning means positioning themselves individually on areas to be cleaned.

42. The method according to claim 41, wherein said cleaning means is moved along a direction from the gum toward the crown of said tooth when said cleaning means is nearer to said longitudinal axis of the tooth.

43. The method according to claim 36, wherein a part of said movement of said cleaning means in said first direction nearer to said longitudinal axis of the tooth extends in a direction from the gum toward the crown of said tooth.

44. The method according to claim 36, wherein cleaning is performed on at least two opposite sides of the teeth.

45. The method according to claim 36, whereby said cleaning means are controlled to contact the gum area at a higher pressure, then being shifted toward a crown of said tooth at said higher pressure, said higher pressure being then lowered in a region of said crown, said cleaning means then being brought back toward the gum area at said lowered pressure.

46. The method according to claim 36 further comprising cyclically moving a further cleaning means within a plane perpendicular to said first axis.

47. The method according to claim 36, whereby cleaning is effected by contacting said tooth with cleaning areas of said cleaning means which individually position themselves due to reaction forces of the tooth.

48. The method according to claim 36, wherein a tooth is contacted on opposite sides with substantially equal contacting pressure of said cleaning means.

49. A method for cleaning teeth, the method comprising the steps of:
applying at least one cleaning means to a tooth to be cleaned;
driving said cleaning means relative to said tooth to be cleaned;
generating a first drive for oscillating substantially along a first axis substantially parallel to a longitudinal axis of a tooth;
generating a second drive oscillating substantially along a second axis perpendicular to said first axis;
superimposing said two oscillating drives along said first and second axis to form a composite drive for the cleaning means along a non-circular path;
applying said composite drive to said cleaning means;
controlling a pressure generated by said cleaning means on the tooth, such that said pressure is greater when said cleaning means moves from a gum to a crown of the tooth than when said cleaning means moves from said crown to said gum.

* * * * *